United States Patent
Kazakov et al.

(10) Patent No.: US 7,943,067 B2
(45) Date of Patent: *May 17, 2011

(54) NANOGELS AND THEIR PRODUCTION USING LIPOSOMES AS REACTORS

(75) Inventors: Sergey Kazakov, White Plains, NY (US); Marian Kaholek, Bloomfield, NJ (US); Kalle Levon, New York, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 1061 days.

This patent is subject to a terminal disclaimer.

(21) Appl. No.: 10/218,554

(22) Filed: Aug. 14, 2002

(65) Prior Publication Data
US 2003/0044455 A1 Mar. 6, 2003

Related U.S. Application Data

(60) Provisional application No. 60/312,878, filed on Aug. 16, 2001.

(51) Int. Cl.
*B01J 13/02* (2006.01)
*C08J 3/28* (2006.01)
*C08F 2/50* (2006.01)

(52) U.S. Cl. ............. 264/4.1; 264/4; 264/4.3; 264/4.33; 264/4.7; 264/4.6; 522/84; 522/86; 522/85; 522/104; 522/113; 522/117; 522/116; 522/120; 522/121; 522/150; 522/154; 522/178; 522/179; 522/182; 428/402; 428/402.21; 428/402.22; 428/402.24; 428/403

(58) Field of Classification Search ........... 424/450, 424/489, 499; 264/4.1–4.6; 428/403, 402, 428/402.21, 402.22, 402.24; 522/84–86, 522/104, 107, 113, 117, 116, 120, 121, 150, 522/153, 154, 178, 179, 182

See application file for complete search history.

(56) References Cited

U.S. PATENT DOCUMENTS

| | | | | |
|---|---|---|---|---|
| 5,314,811 A | * | 5/1994 | Lee et al. | 435/101 |
| 5,464,629 A | * | 11/1995 | Monshipouri et al. | 424/450 |
| 5,573,934 A | * | 11/1996 | Hubbell et al. | 435/177 |
| 5,626,870 A | * | 5/1997 | Monshipouri et al. | 424/450 |
| 6,018,033 A | * | 1/2000 | Chen et al. | 536/4.1 |
| 6,284,375 B1 | * | 9/2001 | Jin et al. | 428/403 |
| 2002/0061336 A1 | * | 5/2002 | O'Connor et al. | 424/499 |

FOREIGN PATENT DOCUMENTS

| | | | |
|---|---|---|---|
| GB | PCT/GB00/00349 | * | 8/2000 |
| WO | WO/97/04787 | * | 2/1997 |
| WO | WO/98/00170 | * | 1/1998 |

OTHER PUBLICATIONS

Commuication for European Patent Application No. 02 766 005.9-2112, dated Jul. 15, 2008 (4 pgs.).

Kim Jin-Chul et al., "Temperature-Sensitivity of Liposomal Lipid Bilayers Mixed with Poly(N-isopropylacrylamide-co-Acrylic Acid)", *Journal of Biochemistry* vol. 121, No. 1, pp. 15-19. (1997).

Alfonso R. Gennaro, Remington: "The Science and Practice of Pharmacy", pp. 919.

* cited by examiner

*Primary Examiner* — James Seidleck
*Assistant Examiner* — Saira Haider
(74) *Attorney, Agent, or Firm* — Frommer Lawrence & Haug LLP

(57) ABSTRACT

The present invention includes a method for preparing polymer hydrogel spherical particles on a nanometer scale (nanogels). The method includes encapsulating hydrogel-forming components into liposomes, diluting the large unilamellar liposomes suspension to prevent polymerization outside the liposomes, and polymerizing the encapsulated hydrogel-forming components. The lipid bilayer may be solubilized with detergent. The phospholipid and detergent molecules and their micelles may then be removed by dialysis. The resulting nanogels may then be dried by evaporation in a temperature gradient. Poly(acrylamide), poly(N-isopropylacrylamide), and poly(N-isopropylacrylamide-co-1-vinylimidazole) hydrogel particles with a diameter from 30 to 300 nm were detected and characterized by dynamic light scattering technique. The solvent, temperature, pH, and ionic sensitivities of the nanogels were studied.

34 Claims, 10 Drawing Sheets

Composition of hydrogel-forming media and properties of macroscopic hydrogels

| Hydrogel | [AAm] (wt%) | [NIPA] (wt%) | [VI] (wt%) | [MBA] (wt%) | [DEAP] (wt%) | Dilution (times) | $\tau_P$ (h) | Sensitivity | $\alpha$ |
|---|---|---|---|---|---|---|---|---|---|
| PAAm | 4.73 | - | - | 0.47 | 0.10 | 20 | 2 | Acetone: 40 vol % | ~0.07 |
| PNIPA | - | 5.10 | - | 0.51 | 0.10 | 20 | 2 | $T_V$~32 °C | ~0.12 |
| PNIPA-VI | - | 5.51 | 1.97 | 0.50 | 0.10 | 25 | 2 | $T_V$~37 °C | ~0.14 |
| PNIPA-VI | - | 5.51 | 1.97 | 0.50 | 0.10 | 25 | 2 | pH | ~6 |

Figure 1

1. Solution of Phospholipid and Anchor-Forming Monomer in Chloroform

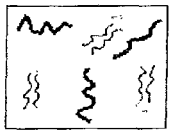

2. Evaporation of Chloroform: Dry Lipid Film Formation

3. Hydration Encapsulation of Hydrogel-Forming Components and MLV Formation

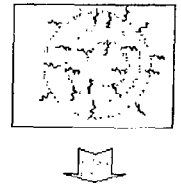

6. Photopolymerization Inside Liposomes UV Illumination

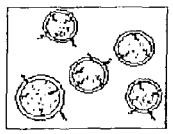

4. Freeze-Thaw Cycles and Sonication: LUV Formation

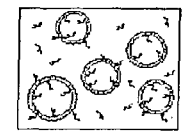

7. Solubilization of the Lipid Bilayer Addition of Detergent

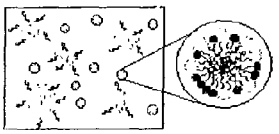

8. Dialysis Removal of the Mixed Micelles

9. Drying Hydrogel Particles Evaporation in Temperature Gradient

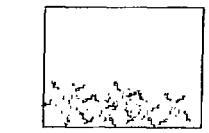

Figure 3

NANOGELS AND THEIR PRODUCTION USING LIPOSOMES AS REACTORS

§0. CLAIM TO PRIORITY

Benefit is claimed, under 35 U.S.C. §119(e)(1), to the filing date of provisional patent application serial No. 60/312,878, entitled "UV-INDUCED GELATION ON NANOMETER SCALE USING LIPOSOME REACTOR", filed on Aug. 16, 2001 and listing Sergey Kazakov, Marian Kaholek, and Kalle Levon as the inventors, for any inventions disclosed in the manner provided by 35 U.S.C. §112, ¶ 1. This provisional application is expressly incorporated herein by reference.

§0.1 FEDERALLY SPONSORED RESEARCH

This invention was made with Government support and the Government has certain rights in the invention as provided for by contract number 0660076225 awarded by DARPA.

§1. BACKGROUND

§1.1 Field of the Invention

The present invention concerns nanogels and producing nanogels in general. In particular, the present invention concerns nanogel production using liposomes as reactors.

§1.2 Related Art

Hydrogels are networks of hydrophilic polymers that can be swollen with water. They exhibit both liquid properties (because the major constituent is water) and solid properties (because of crosslinking during polymerization). Further, depending on monomers incorporated into the network, the system becomes sensitive to environmental conditions such as pH, temperature, ion concentration, electric and magnetic fields, light and solvent. This sensitivity is evidenced in the polymer network's capacity to swell or shrink in response to changes in its environment.

Artificial systems of spherical hydrogel particles have already found a variety of biomedical applications in drug delivery, drug targeting, protein separation, enzyme immobilization, etc.

It has been reported that some polymer gels can swell or shrink discontinuously and reversibly in response to many different stimuli (temperature, pH, ions, electric fields or light) depending on the chemical composition of the gel/solvent system. The volume change can be as large as a thousand-fold. Unfortunately, however, macroscopic gels respond to the environmental changes on a rather long time scale. The article Tanaka et al., *J. Chem. Phys.*, 90: 5161 (1989) (This article is incorporated herein by reference.) showed that for a spherical gel, the time required for swelling or shrinking is inversely proportional to the square of its radius. Therefore, decreasing the size of a spherical hydrogel should reduce the time needed for shrinking and/or swelling. A decrease in the hydrogel size to nanometer scale, and the expected quick swell and/or shrink times of such nanometer scale hydrogels should greatly widen potential applications for hydrogels.

Work related to preparing and characterizing submicrometer-scale hydrogel particles has intensified recently (See, e.g., the articles: R. Pelton, *Adv. Coll. Interface Sci.*, 85: 1-33 and the references therein (2000); T. Tanaka et al., *Phys. Rev. Lett.*, 45: 1636 (1980); G. M. Eichenbaum et al., *Macromolecules*, 31: 5084 (1998); G. M. Eichenbaum et al., *Macromolecules*, 32: 4867 (1999); G. M. Eichenbaum et al., *Macromolecules*, 32: 8996 (1999); P. Markland et al., *J. Biomed. Mater. Res.*, 47: 595 (1999); C. Wu, *Polymer*, 39: 4609 (1998); K. Kratz et al., *Polymer*, 42: 6631 (2001); M. Monshipouri et al., U.S. Pat. No. 5,626,870 (1997), hereafter referred to as "the Monshipouri Patent"; V. P. Torchilin et al., *Macromol. Chem., Rapid Commun.* 8: 457 (1987), hereafter referred to as "the Torchilin article"; K. Gao et al., *Biochim. Biophys. Acta*, 897: 337 (1987); T. Jin et al., *FEBS Lett.*, 397: 70 (1996); P. F. Kiser et al., *Nature*, 394: 459 (1998). These articles and the patent are incorporated herein by reference). However, in all the referenced works (except the Monshipouri Patent and the Torchilin article) the sizes of hydrogel particles varied on the micrometer scale. (In these works, optical or electron microscopy was used for characterization.)

Liposomes, or lipid vesicles, are phospholipid assemblies of a flexible, cell membrane-like lipid bilayer, the surface of which acts as a permeability barrier. Liposomes may differ in size (small or large) and lamellarity (multilamellar or unilamellar), resulting in liposomal suspensions of multilamellar vesicles (MLV), large unilamellar vesicles (LUV), or small unilamellar vesicles (SUV). Liposomes have completely closed lipid bilayer membranes containing an entrapped aqueous volume. This structure provides the conditions for using the liposomal interior as a reaction vessel for carrying out chemical or biochemical reactions since different compounds may be trapped in the liposome. For example, liposomes may be employed as reactors for nanometer-scale reactions such as hydrogel production.

The size of hydrogels produced in liposomes is dependent on the sizes of the liposomes themselves. U.S. Pat. No. 5,626,870 (hereafter "the Monshipouri patent") describes hydrogels with sizes ranging from 50-3000 nm. The Torchilin article describes hydrogel-containing liposomes with average diameter of about 650 nm. Liposomes used to produce hydrogels with this range of diameters may be multilamellar (d>1000 nm) or unilamellar (LUV: 100 nm <d<1000 nm; or SUV: d<100 nm). Production of each class of liposomes required different methods of preparation, such as hydrodynamic shear (U.S. Pat. No. 5,082,664), reverse phase evaporation (U.S. Pat. No. 4,235,871), sonication (U.S. Pat. No. 4,089,801), detergent dialysis (*Proc. Nat. Acad. Sci. USA*, 1979, 145-149), and extrusion through membrane pores (U.S. Pat. No. 5,008,050). These methods, however, make it difficult to control liposome size on a large scale and often result in a loss of material, causing low liposome yields.

The Monshipouri patent prepared LUV liposomes with diameters of about 800 nm using extrusion through 800-nm membranes. Using the extrusion technique, only LUV can be prepared, material can be lost, and it is highly time- and labor-consuming.

The Torchilin article describes preparing LUV liposomes with average diameters of about 650 nm using the reverse phase evaporation method. Using this technique, it is difficult to control liposome size and polydispersity, which is why the authors presented only the average sizes of the particles detected by dynamic light scattering. Moreover, gel containing liposomes and gel particles were not distinguished by scanning electron microscopy.

Centrifugation, filtration and column chromatography have been used to prevent polymerization outside the liposomes, and to remove extra-liposomal initiator (such as calcium ions in the Monshipouri patent) or to separate the monomer-containing liposomes from the extra-liposomal non-entrapped monomer (the Torchilin article). However, these methods result in a loss of phospholipid, and thus have low yields of unilamellar liposomes.

After polymerization, detergent/phospholipid mixed micelles may be removed by centrifugation, as in the Monshipouri patent. A drawback to this technique is that a portion of hydrogel particles can be lost during centrifugation. In the Torchilin article, the detergent and phospholipid were not removed at all.

Furthermore, the Monshipouri patent describes a limited number of hydrogel-forming substances including sodium alginate, chitosan, and K-carrageenan and uses physical polymerization, which requires an initiator of gelation for which a liposomal bilayer is permeable. However, removing these initiators by centrifugation, filtration, or column chromatography results in loss of phospholipid and consequently low yields of unilamellar liposomes. The Torchilin article describes one composition of a hydrogel-forming medium. The presence of initiator (4,4'-azobis(4-cyanovaleric acid)) and accelerator (N,N,N',N'-tetramethylenediamine, TEMED) indicates the use of redox polymerization, which can proceed without UV-irradiation. There are no compositional details and parameters of polymerization. Moreover, the Torchilin article uses a gel permeation chromatography to prevent polymerization outside the liposomes, which results in loss of monomer-loaded liposomes. Also, the Monshipouri patent and the Torchilin article deal only with aqueous suspensions of hydrogel particles and does not consider producing dry hydrogel particles or delivering water-insoluble compounds into the liposomal reactor.

In view of the limits of the state of the art, hydrogel nanoparticles (nanogels), and methods for their production, are needed.

§2. SUMMARY OF INVENTION

The present invention describes hydrogels with nanometer-scale diameters (nanogels), as well as methods for producing such nanogels.

The present invention may produce hydrogel particles of nanometer dimensions, using liposomes as reactors, by (i) encapsulating hydrogel-forming components into the liposomes and (ii) polymerizing the encapsulated hydrogel-forming components.

The present invention considers new methods and procedures for providing polymerization and cross-linking reactions (gelation) in a liposomal interior to fabricate hydrogel nanoparticles (nanogels) for a broad spectrum of applications such as drug delivery, nanofilm deposition, and fabricating nanodevices, biosensors, compact reporter systems.

It is important that the methods used to prepare liposomes and hydrogels (especially in large-scale processing) are size-processing and the yield of nanoparticles should be maximal.

In a preferred embodiment of the present invention, a liposomal suspension containing hydrogel-forming components may be diluted before polymerization to prevent polymerization outside the liposomes. After polymerization, the lipid bilayer may be separated from the hydrogels (e.g., using detergent), the resulting mixed phospholipid-detergent micelles removed (e.g., by dialysis), and hydrogel particles dried (e.g., by gentle evaporation in temperature gradient).

§3. BRIEF DESCRIPTION OF DRAWINGS

FIG. 1 is a table that lists the composition of hydrogel-forming media and properties of macroscopic hydrogels studied.

FIGS. 2a-2d include graphs that show size distribution curves for liposomes prepared in various manners.

FIG. 3 schematically presents the steps of hydrogel nanoparticle preparation including the possibility of modifying the surface of the nanogels.

FIGS. 4a and 4b show Atomic Force Microscopy (AFM) images (amplitude data) of a PNIPA-VI lipobead after gelation inside liposomes (a) (frame 400×400 nm$^2$; 1, flattened lipid bilayer; 2, nanogel; See FIG. 3, Step 6), and mixed phospholipid/detergent micelles and a nanogel after lipid bilayer solubilization (b) (frame 440×440 nm$^2$; 1, nanogel; 2, mixed micelles; See FIG. 3, Step 7).

Figure 9:
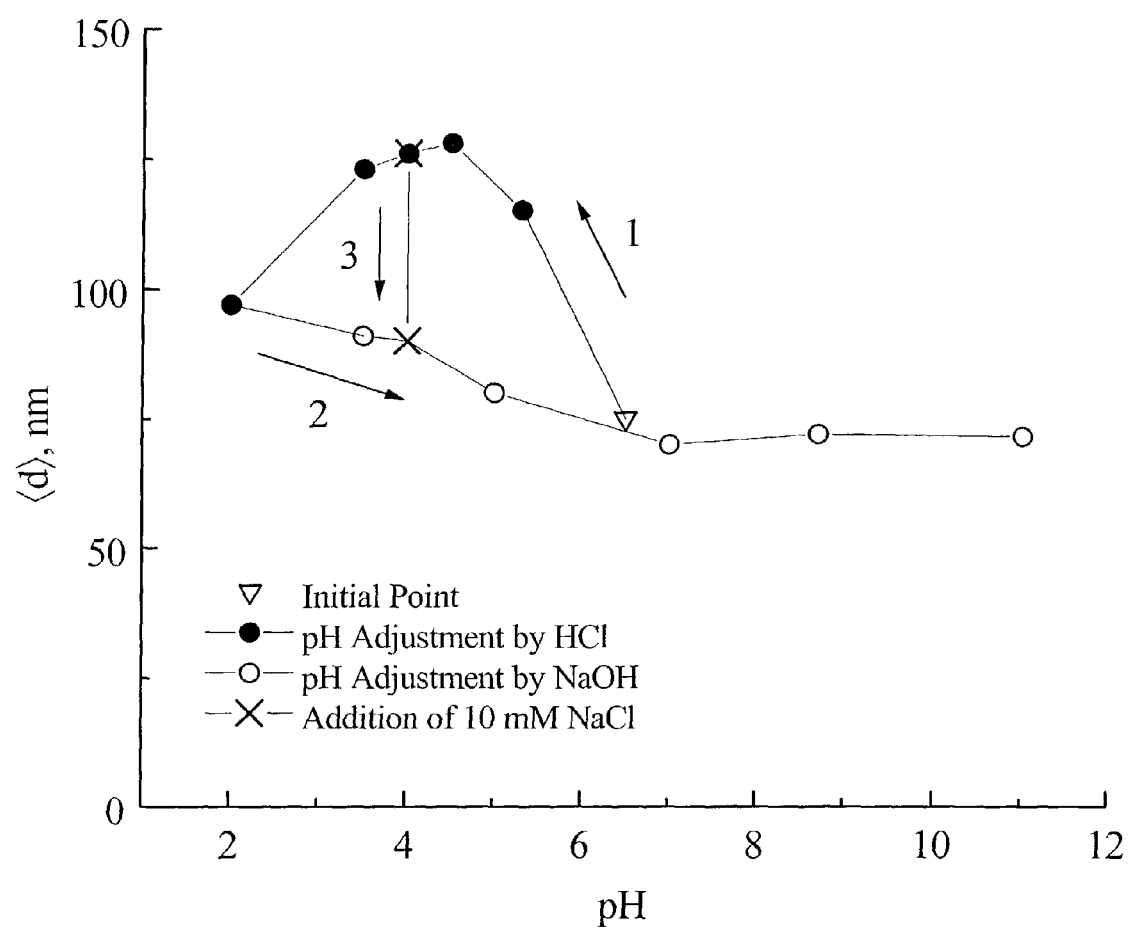
Figure 10:
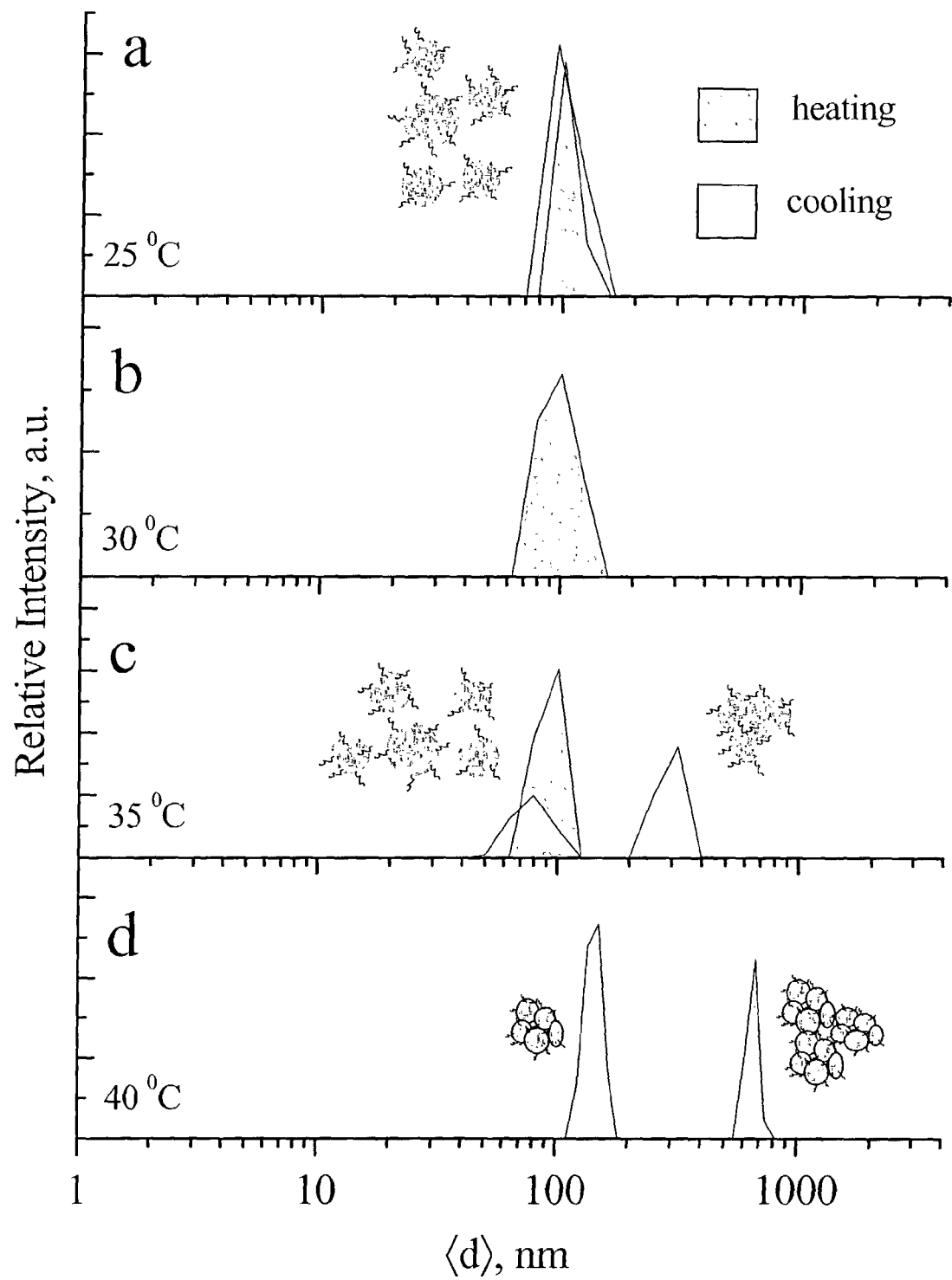

FIG. 9 is a graph showing the pH dependence of the average diameter of PNIPA-VI nanogels as pH was decreased by adding 0.1 M HCl, increased by adding 0.2 M NaOH, as well as the change of the nanogels' size after adding 10 mM NaCl at pH 4.0.

FIGS. 10a-10d are graphs showing the effect of temperature on the collapse and subsequent aggregation of PNIPA-VI nanogels for pure PNIPA-VI nanogels in water at temperatures below, and at a temperature above, the volume phase transition temperature.

§4. DETAILED DESCRIPTION

The present invention concerns nanogels and their production. The following description is presented to one skilled in the art to make and use the invention, and is provided in the context of particular embodiments and methods. Various modifications to the disclosed embodiments and methods will be apparent to those skilled in the art, and the general principles set forth below may be applied to other embodiments, methods and applications. Thus, the present invention is not intended to be limited to the embodiments and methods shown and the inventors regard their invention as the following disclosed methods, apparatus and materials and any other patentable subject matter to the extent that they are patentable.

The present invention uses liposomes as reactors in which hydrogel particles with nanometer-scale radii can be produced. As described in §4.1 below, liposomes may be prepared by freeze/thawing and a combination of centrifugation and extrusion or sonication and filtration. Then, as described in §4.2 below, hydrogel-forming components are put inside the liposomes and polymerization and gelation take place by photoinitiation. After hydrogel formation, the hydrogel particles can be separated from the liposomes and further processed as described in §4.2 below. As described in §4.3 below, the resulting hydrogel particles have nanometer-scale diameters and demonstrate the ability to swell or shrink in response to changes in their environment, such as the temperature.

§4.1 PREPARING LIPOSOMES TO BE USED AS REACTORS

The present invention uses liposomes as reactors inside which hydrogel particles of a nanoscale range are synthesized. Another use for liposomal reactors may be to use the interlayer space of the phospholipid bilayer as a container for water-insoluble components of the polymerization reaction. These water-insoluble reagents should be introduced into the interlayer container on the stage of lipid bilayer dry film formation.

Preparing a liposomal solution of large unilamellar vesicles (LUVS) using a conventional procedure (See, e.g., G. Gregoriadis, *Liposome technology*, Vol. III, $2^{nd}$ edn, CRC Press: Boca Raton, Fla. (1994). This book is incorporated herein by reference.) includes freezing-thawing and extruding a multilamellar vesicle (MLV) suspension. Unfortunately, it is time- and labor-consuming, and leads to a low concentration of liposomes. Preparing small unilamellar vesicles (SUVs) using another conventional procedure does not contain freezing and thawing steps—only sonication. However, sedimentation of a sonicated SUV suspension results in a much lower concentration of liposomes in a final solution. As noted earlier, other methods of liposome preparation such as hydrodynamic shear (U.S. Pat. No. 5,082,664), reverse phase evaporation (U.S. Pat. No. 4,235,871), sonication (U.S. Pat. No. 4,089,801), detergent dialysis (*Proc. Nat. Acad. Sci. USA*, 1979, 145-149), and extrusion through membrane pores (U.S. Pat. No. 5,008,050) have difficulty in controlling liposomal size in large scales and may have low yields due to loss of material.

One alternative to these conventional methods is to avoid extrusion, filtration, and centrifugation during any step of liposome preparation and instead use probe sonication after freezing and thawing to prevent a loss of the phospholipid and to gain a high yield of monodisperse liposomes. Using this method either LUV or SUV in the range from 30 to 1000 nm may be prepared. Multilamellar liposomes with diameters higher than 1000 nm may be obtained during the stage of phospholipid dry film hydration. Regulating the power of the sonifier and the sonication time provides a method to control the average size and polydispersity of liposomes and hence the size and polydispersity of nanogels. An example of this alternative technique of liposome production is provided below.

A needed volume of EPC/chloroform solution with concentration 20 mg/ml of phospholipid was poured into a round-bottomed flask. The chloroform was evaporated under flashing with nitrogen to form a lipid film. The film was held under vacuum for at least 3 h and then hydrated by dispersing in 50 mM Tris-HCl (pH 7.5). The volume of the buffer was chosen to provide a final concentration of 5 mg/ml EPC. After gentle handshaking and total dispersion of lipid, multilamellar vesicles were obtained. The mixture was frozen in dry ice/acetone (−77° C.) and then thawed (25° C.). This freezing and thawing was repeated at least five times. Large unilamellar liposomes were prepared by long-time sonication (Ultrasonic Cleaner 50D, VWR Scientific Products, West Chester, Pa., USA) of a milky MLV suspension in a water bath at 20-100 W for 1 hour until the sample became transparent. Under specified conditions (power and duration of sonication) all liposome preparations had a unimodal size distribution within the range of average sizes from 30 to 300 nm.

Figure 2:
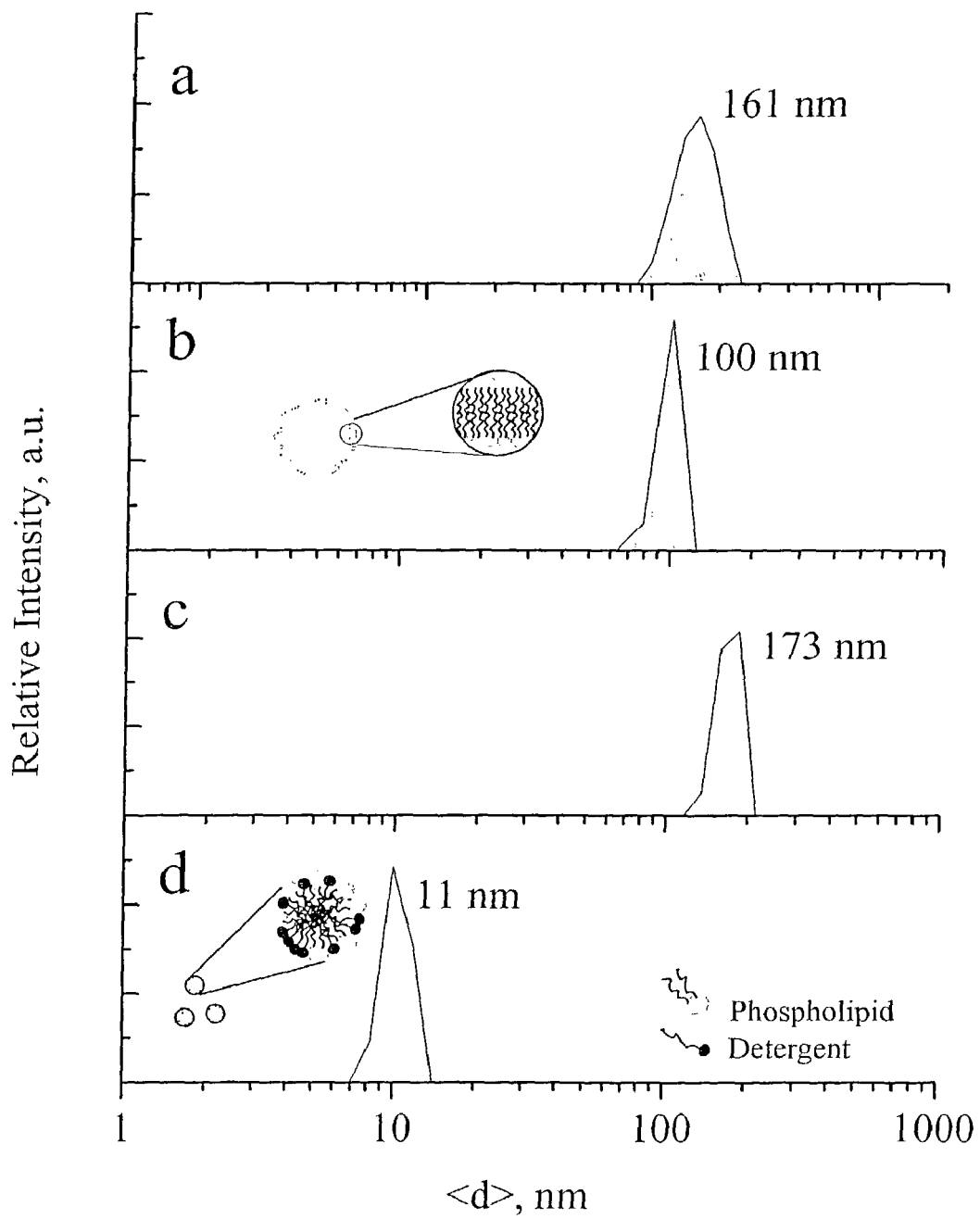

The size distribution curves for pure (or solvent filled) EPC liposomes are provided in FIGS. 2a-2d. As shown in FIG. 2a, the curve for liposomes prepared by extrusion through two stacked polycarbonate membranes with 100 nm pores 11 times exhibited a wide monomodal distribution with a peak at 161 nm. This method of liposome preparation was time-consuming and a large amount of phospholipid was lost during the extrusion. In general, as shown in FIGS. 2b and 2c, the curves for liposomes sonicated for one hour exhibited a narrower unimodal size distribution. A z-average hydrodynamic diameter <d> depends on the power of the sonifier. The width of the distribution could be governed by the duration of sonification. The size distribution curves for liposomes sonicated at 60 W and 20 W are presented in FIGS. 2b and 2c, respectively. At the conditions used to prepare liposomes (see above) the liposomes with an average diameter between 30 and 300 nm were reliably detected. The method provided a higher concentration of liposomes and therefore a higher concentration of hydrogel particles due to no loss of phospholipid.

Phospholipids with liquid crystal phase transition temperatures from −20 to +74° C. may be used for liposome formation, such as egg yolk L-α-phosphatidylcholine ("EPC"), 1,2-dimyristoyl-sn-glycero-3-phosphatidylcholine ("DMPC"), 1,2-dipalmitoyl-sn-glycero-3-phosphatidylcholine ("DPPC"), 1,2-dioleoyl-sn-glycero-3-phosphatidylcholine ("DOPC"), 1,2-distearoyl-sn-glycero-3-phosphatidylcholine ("DSPC"), 1,2-dilauroyl-sn-glycero-3-phosphatidylcholine ("DLPC"), 1,2-dioleoyl-sn-glycero-3-phosphaethanolamine ("DOPE"), 1-palmitoyl-2-oleoyl-sn-glycero-3-phosphaethanolamine ("POPE"), 1,2-dimyristoyl-sn-glycero-3-phosphaethanolamine ("DMPE"), 1,2-dipalmitoyl-sn-glycero-3-phosphaethanolamine ("DPPE"), and 1,2-distearoyl-sn-glycero-3-phospharthanolamine ("DSPE"). These phospholipids may be mixed with a sterol, such as cholesterol, to stabilize the phospholipid bilayer.

§4.2 GENERATING NANOGELS USING LIPOSOMES AS REACTORS

Preparing hydrogel particles of nanometer dimensions, using liposomes as reactors, includes the following general steps: (i) encapsulating the hydrogel-forming components into the liposomes and (ii) polymerizing hydrogel-forming components. Polymerization outside the liposomes may be prevented (e.g., by dilution). After polymerization, the lipid bilayer can be separated from hydrogels (e.g., by using detergent to solubilize the liposome). The mixed phospholipid-detergent micelles may be removed (e.g., by dialysis), and hydrogel particles may be dried (e.g., by gentle evaporation in a temperature gradient). FIG. 3 delineates the steps of hydrogel formation using liposomes as reactors.

§4.2.1 ENCAPSULATION OF HYDROGEL PRECURSORS

Hydrogel-forming components may be introduced into liposomes if lipids are dispersed in a solution containing monomer, crosslinker, and photoinitiator in 50 mM Tris-HCl (pH 7.5) instead of pure buffer during liposome formation. After freeze-thaw cycles and sonication of the MLV solution, the content of the LUVs' interior and exterior are identical.

§4.2.2 PREVENTING POLYMERIZATION OUTSIDE OF LIPOSOMES

After hydrogel precursors are entrapped in the liposome's interior, the composition of the medium inside and outside the liposome is the same. To prevent the hydrogel-forming components outside of the liposome from polymerizing, the liposome solution may be diluted. The optimal dilution of the LUV suspension for PAA and PNIPA gels was twenty-fold, and for PNIPA-VI gels it was twenty-five-fold (FIG. 1, column 7).

An alternate method for preventing polymerization outside liposomes is to use polymerization inhibitors such as hydroquinone ("HQ"), hydroquinone monomethylether ("MEHQ"), or N,N'-di-sec-butyl-p-phenylenediamine in the LUV solution.

Centrifugation, filtration and column chromatography may also be used to prevent polymerization outside the liposomes. However, these methods typically result in a loss of phospholipid and have low yields of unilamellar liposomes.

§4.2.3 POLYMERIZATION

Gelation in liposomes may be performed by chemical (radical) or physical mechanisms. Types of radical polymerization include redox and photopolymerization. Different mechanisms require different monomers and initiators in hydrogel-forming solution.

Water-soluble photoinitiators or redox initiators may initiate radical polymerization. For all types of radical polymerization the following cross-linkers may be used: N,N'-methylenebisacrylamide, N,N'-(1,2-dihydroxyethylene) bisacrylamide, ethylene glycol diacrylate, di(ethylene glycol) diacrylate, tri(ethylene glycol) diacrylate, tetra(ethylene glycol) diacrylate, ethylene glycol dimethacrylate, di(ethylene glycol) dimethacrylate, tri(ethylene glycol) dimethacrylate, tetra(ethylene glycol) dimethacrylate, and pentaerythritol triacrylate. For radical polymerization initiated by either method, monomers containing a vinyl-group or a mixture including such monomers should be used. Such monomers include acrylamide, N-isopropylacrylamide, N,N-dimethylacrylamide, N,N-diethylacrylamide, 1-vinylimidazole, sodium acrylate, sodium methacrylate, 2-hydroxyethyl methacrylate ("HEMA"), N,N-dimethylaminoethyl methacrylate ("DMAEMA"), N-[tris(hydroxymethyl)methyl]acrylamide, 1-(3-methacryloxy)propylsulfonic acid (sodium salt), allylamine, N-acryloxysuccinimide, N-vinylcaprolactam, 1-vinyl-2-pyrrolidone, 2-acrylamido-2-methyl-1-propanesulfonic acid (sodium salt), (3-acrylamidopropyl) trimethylammonium chloride, and diallyldimethylammonium chloride.

Biocompatible hydrogels may be prepared from a hydrogel-forming medium containing the following biocompatible polymers: methacrylated or hydroxyethyl-methacrylated water soluble non-ionic or ionic polysaccharides (For example, methacrylated dextran ("dex-MA"), hydroxyethyl-methacrylated dextran ("dex-HEMA"), methacrylated pullulan, and hydroxyethyl-methacrylated pullulan), poly(ethylene glycol) monomethacrylate, or poly(ethylene glycol) diacrylate).

Biodegradable hydrogels may be prepared from a hydrogel-forming medium can containing the following biodegradable polymers: triblock copolymer of poly(lactic acid)-poly(ethylene glycol)-poly(lactic acid) end-capped with acrylate or methacrylate functionalities, grafted copolymers of poly(lactic acid)-poly(vinyl alcohol) end-capped with acrylate or methacrylate functionalities, and (oligolactate)-hydroxyethyl methacrylated dextran [dex-(lactate-)HEMA].

Photopolymerization occurs at room temperatures (10-25° C.) and may produce a broad spectrum of hydrogels that may be responsive to temperature, pH, ions, electric and magnetic fields, light, and certain types of solvents. Photopolymerization facilitates the use of liposomes as reactors and induces gelation (time scale: minutes). The following may function as photoinitiators: 2,2-diethoxyacetophenone, 2,2-dimethoxy-2-phenylacetophenone (IRGACURE 651), 1-[4-(2-hydroxyethoxy)phenyl]-2-hydroxy-2-methyl-1-propan-1-one (IRGACURE 2959), 2-hydroxy-2-methylpropiophenone, and 2-hydroxy-4'-(2-hydroxyethoxy)-2-methylpropiophenone.

Redox polymerization, on the other hand, occurs at high temperatures (50-70° C.) and is relatively slow (time scale: hours). The following may function as redox initiators: ammonium persulfate, potassium persulfate, 2,2'-azobis[2-methyl-N-(2-hydroxyethyl)propionamide (VA-086), 2,2'-azobis(2-amidinopropane)dihydrochloride (V-50), 4,4'-azobis(4-cyanovaleric acid).

Physical polymerization is also possible in a liposomal reactor but it is limited because it requires specific hydrogel-forming substances that use an initiator of gelation for which a liposomal bilayer is permeable.

In comparison to the method proposed in the Monshipouri patent, which uses physical polymerization, the present invention uses chemical polymerization. For example, in a preferred embodiment of the present invention adding a photoinitiator into the liquid medium inside each liposome and exposing it to UV light may be used to initiate polymerization and crosslinking within the liposomal reactor.

§4.2.4 SOLUBILIZATION OF LIPID BILAYER COVERING HYDROGEL PARTICLES

After polymerization inside the liposomes, bare hydrogel particles may be obtained by dispersing the lipid bilayer. Detergents are widely used for this purpose (O. Lopez et al., *Langmuir*, 15: 4678 (1999), hereafter called "Lopez et al.", and D. B. Datta, *A Comprehensive Introduction to Membrane Biochemistry*, Floral Publishing, Madison (1987). This article and book are both incorporated herein by reference). When detergents are used, the micelle-forming amphiphiles compete with the bilayer lipids to dissolve the bilayer into the amphiphile micelles. At low detergent/lipid ratios, each detergent molecule adsorbs onto the bilayers (Lopez et al.). With an increasing detergent/lipid ratio, the amount of the detergent on the bilayer increases until the detergent breaks up the bilayer into many mixed micelles of lipid-detergents. A further increase in the detergent/lipid ratio leads to delipidation of the lipid-detergent mixed micelles. Adding 15 to 50 mM of Triton X-100 ($T_{X-100}$) into the solution of liposomes results in disappearance of the peak at 100 nm and appearance of a new peak at 9.9 nm (FIG. 2d). Lopez et al. showed that the size distribution curves for micellar $T_{X-100}$ solutions presented a monomodal distribution with a peak at 9 nm, whereas for the mixture of 2 mM $T_{X-100}$ and liposomes they obtained the average diameter of mixed micelles around 17 nm. An intermediate micellar diameter was observed, because the size of mixed micelles depends on the concentration of the phospholipids. The latter increases the size of the micelles.

When the lipid bilayer is solubilized, phospholipid/detergent micelles are formed and the bare hydrogel particles are released. Solubilization may be accomplished using non-ionic detergents such as Triton X-100, n-octyl-b-D-glucopyranoside, n-octyl-tetraoxyethylene ("POE4"), n-hexyl-glucopyranoside, and n-heptyl-glucopyranoside, or ionic detergents such as cholic acid (sodium salt), glycocholic acid (sodium salt), deoxycholic acid (sodium salt), taurocholic acid (sodium salt), chenoxycholic acid (sodium salt), and sodium dodecyl sulfate ("SDS").

Phospholipases such as phospholipase $A_2$ ($PLA_2$), phospholipase C (PLC) or phospholipase D (PLD) may be used to solubilize the phospholipid bilayer, but this method is expensive.

§4.2.5 REMOVAL OF MICELLES

Mixed phospholipid-detergent micelles may be removed by dialysis. In one embodiment of the invention (PNIPA hydrogels), dialysis is performed against water for seven days. Dialysis against water removes mixed micelles without decreasing nanogel yield. Centrifugation, filtration, and chromatography may also be used to remove micelles, but hydrogel particles may be lost in the process, resulting in low yields.

§4.2.6 DRYING OF HYDROGEL PARTICLES

After being separated from micelles, hydrogel particles may be dried to increase their concentration. Hydrogel particles may be dried by evaporating water in a temperature gradient under vacuum and flashing with nitrogen. An alternative method of drying hydrogel particles is freeze-drying (lyophilic drying). The dried hydrogel particles may be dissolved in an appropriate volume of water for a higher concentration of hydrogel.

§4.3 EXAMPLES OF NANOGELS GENERATED

The syntheses and characterizations of three exemplary embodiments of the present invention are described below. Synthesizing PNIPA, PNIPA-VI, and PAAm nanogels is described in §4.3.1, and their characteristics are described in §4.3.2.

§4.3.1 SYNTHESIS OF PNIPA, PNIPA-VI, AND PAAm NANOGELS

Hydrogels poly(N-isopropylacrylamide) (PNIPA), poly(N-isopropylacrylamide-co-1-vinylimidazole) (PNIPA-VI), and poly(acrylamide) (PAAm) were prepared by photopolymerization. The procedure of UV-induced polymerization included a photoinitiator (such as those listed in §4.2.3) into the content of a liquid hydrogel-forming medium entrapped in the liposomal microreactor. A Blak Ray (365 nm, 100 W) mercury lamp was used as a UV light source to initiate polymerization. The temperature (20° C.) was below the lower critical volume phase transition temperature ($T_V$) for PNIPA and PNIPA-VI. Polymerization time ($\tau_P$) and macroscopic properties (swelling/deswelling ability $\alpha=(R/R_0)^3$, where R is a size in a swollen or shrunken state, and $R_0$ is a size in the prepared state) of a gel depend on various parameters, such as (i) the content of monomer/crosslinker mixture, (ii) the photoinitiator, and (iii) light intensity. To prevent polymerization and gelation in the liposomes' exterior, the extent of dilution should be evaluated (See FIG. 1, column 7).

To optimize the aforementioned parameters, bulky (macroscopic) hydrogels of different compositions were synthesized. At high monomer and/or crosslinker concentrations, the swelling/deswelling ability of the gel was small, whereas at low concentrations the gel was so soft that two pieces of the gel coalesced and could not be separated upon their contact (the latter property was comprehensive for the preparation of monodisperse nanogel solutions). Acceptable ranges of components for preparing an aqueous hydrogel-forming medium are 4.5-15 wt. % monomer or mixture of monomers, 0.1-1 wt. % cross-linker, and 0.05-0.5 wt. % initiator. Additionally, a preferred composition of the three types of hydrogel-forming media and properties of the macroscopic hydrogels that were used for nanogel production are shown in FIG. 1.

Figure 4:
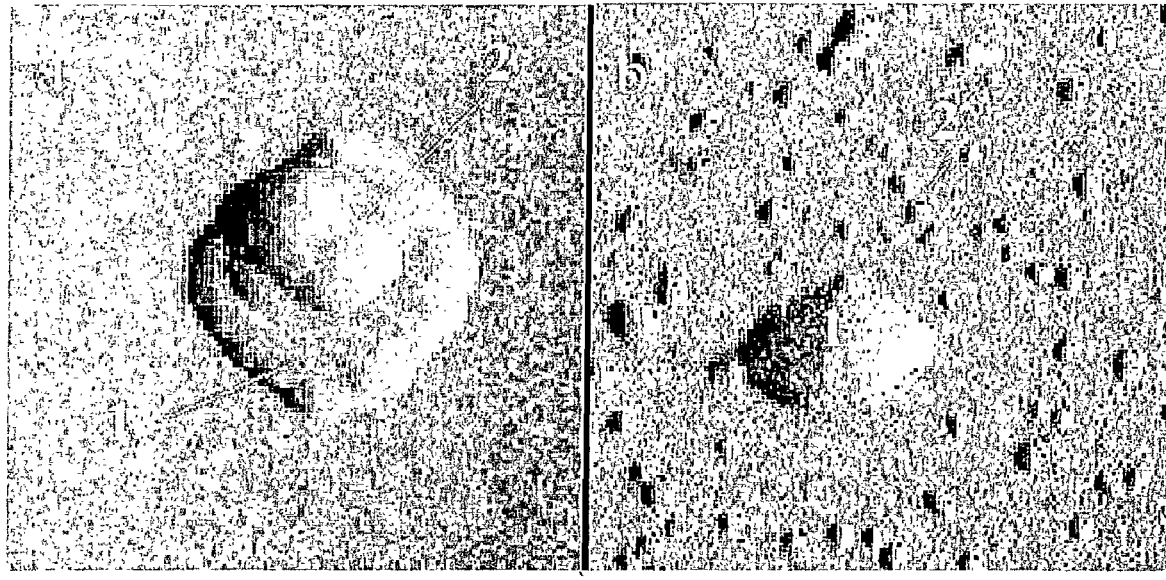

To prepare pre-gel medium-entrapping liposomes, a mixture of a monomer, a cross-linker, and a photoinitiator (See FIG. 1) in 50 mM Tris-HCl (pH 7.5), instead of pure buffer, was used on the hydration stage to disperse the lipids. After freezing-thawing and sonication of multilamellar vesicle (MLV) solution, the content of the interior and exterior of LUVs is identical. The LUV suspension was diluted 20-25 fold by 50 mM Tris-HCl buffer to prevent polymerization in the exterior of the liposomes. No increase in light scattering intensity during transition through 32° C. for PNIPA or through 37° C. for PNIPA-VI was detected, although it was well known that a concentration of the polymers as low as ~0.01 mg/ml caused remarkable opalescence during a liquid-liquid phase transition. Further UV exposure (A. Reiser, *Photoreactive Polymers. The Science and Technology of Resists*, John Wiley & Sons: New York (1989). This book is incorporated herein by reference.) of the solution initiated a free radical polymerization, leading to gelation in the liposomal reactor. Hydrogel particles were within the spherical phospholipid bilayer (See FIG. 4a).

PNIPA-VI is an example of a hydrogel particle with hydrophobic modification of its surface. In general, hydrophobic compounds with a long hydrocarbon tail cannot be introduced directly into the liposome because of their insolubility in water. To overcome this difficulty and introduce an insoluble but reactive component into the liposome, the anchoring monomer was added into the phospholipid/chloroform solution at the step of MLV formation. After preparing unilamellar liposomes, hydrophobic anchors were apparently incorporated into the lipid bilayer.

The experimental procedure for preparing hydrogel particles with hydrophobic anchors attached to their surface was essentially the same as the preparation of unanchored nanogels except that the hydrophobic compound, N-octadecylacrylamide (ODAm), was dissolved in the initial phospholipid/chloroform solution. The amount of ODAm added had a phospholipid to ODAm mole ratio equal to 70:1. This ratio provides the maximal loading capacity of the lipid bilayer (See, e.g., the articles: M. Zignati et al., *Biochim. Biophys. Acta*, 1463: 383 (2000); H. Ringsdorf at al., *Angew. Chem. Int. Ed. Engl.*, 30: 315 (1991); A. Watts et al., *Biochemistry*, 17: 1792 (1978); C. Huang et al., *Proc. Natl. Acad. Sci. USA*, 75: 308 (1978). These articles are incorporated herein by reference.). Hydrophobic monomers of ODAm were incorporated into the structure of the lipid bilayer during the dry lipid film formation step. After LUV formation, free ODAm (insoluble in water) was removed by filtration through a 0.45 μm filter. During UV exposure the PNIPA-VI-co-ODAm copolymer was assumed to form the following structure:

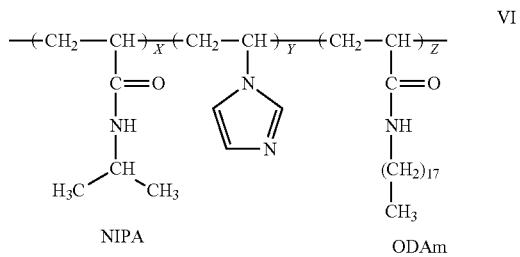

The other steps of preparation were the same as those for preparing unanchored hydrogel particles.

Hydrophobic chains covalently attached to the surface of nanogels during gelation may function as anchors for binding the nanogels with other surfaces such as lipid membranes. Thus, hydrophobic chains increase nanogels' compatibility with lipid bilayers, stabilizing biological membranes. The chains may contain functional groups (ligands) capable of functioning as receptors for specific recognition of analytes. Or, the chains may act as linkers for other functional groups.

To obtain bare hydrogel particles, the phospholipid was removed by adding 15 mM $T_{X-100}$ (critical micelle concentration=0.15 mM (Lopez et al.)). Mixed phospholipid/detergent micelles were formed (See FIG. 4b) and eventually removed by dialysis in SpectraPore 25 kDa membrane bags against water for 7 days with changing water twice a day. The aqueous solution of nanogels had a relatively low level of light scattering intensity because of a low refractive index difference with water. Concentration of the hydrogel nanoparticles was increased by evaporation of water in temperature gradient (from +30° C. to −77° C.) under vacuum and flashing with nitrogen. Dried hydrogel particles were dissolved in a volume of water necessary for reconstitution. The solutions of hydrogel particles of different polymer types were used in DLS characterization.

§4.3.2 CHARACTERIZATION OF PNIPA, PNIPA-VI, AND PAAm NANOGELS

Dynamic light scattering was used to characterize the nanogel systems. Dynamic light scattering measurements were done with a N4 Plus particle size analyzer (Beckman-Coulter, Fullerton, Calif.). A He—Ne laser operating at 628 nm wavelength and 10 mW output power was used as a light source. The scattering angle was held constant at 90°. The temperature was controlled within ±0.1° C. from the set temperature. Solutions were filtered into a square glass cuvette (10 mm) using a 0.45 µm Millipore Millex filter. The quality of measurements was checked over the signal-to-noise ratio, the overflow counts, and the baseline error. When the field-field correlation function was close to single-exponential the cumulative analysis was used. The particle size distribution and average particle size were obtained from the correlation function by CONTIN analysis using standard software supplied by Beckman-Coulter.

Characterizations of the PAAm, PNIPA, and PNIPA-VI nanogels are described in §§4.3.2.1, 4.3.2.2, and 4.3.2.3, respectively.

§4.3.2.1 PAAm NANOGEL

Figure 5:
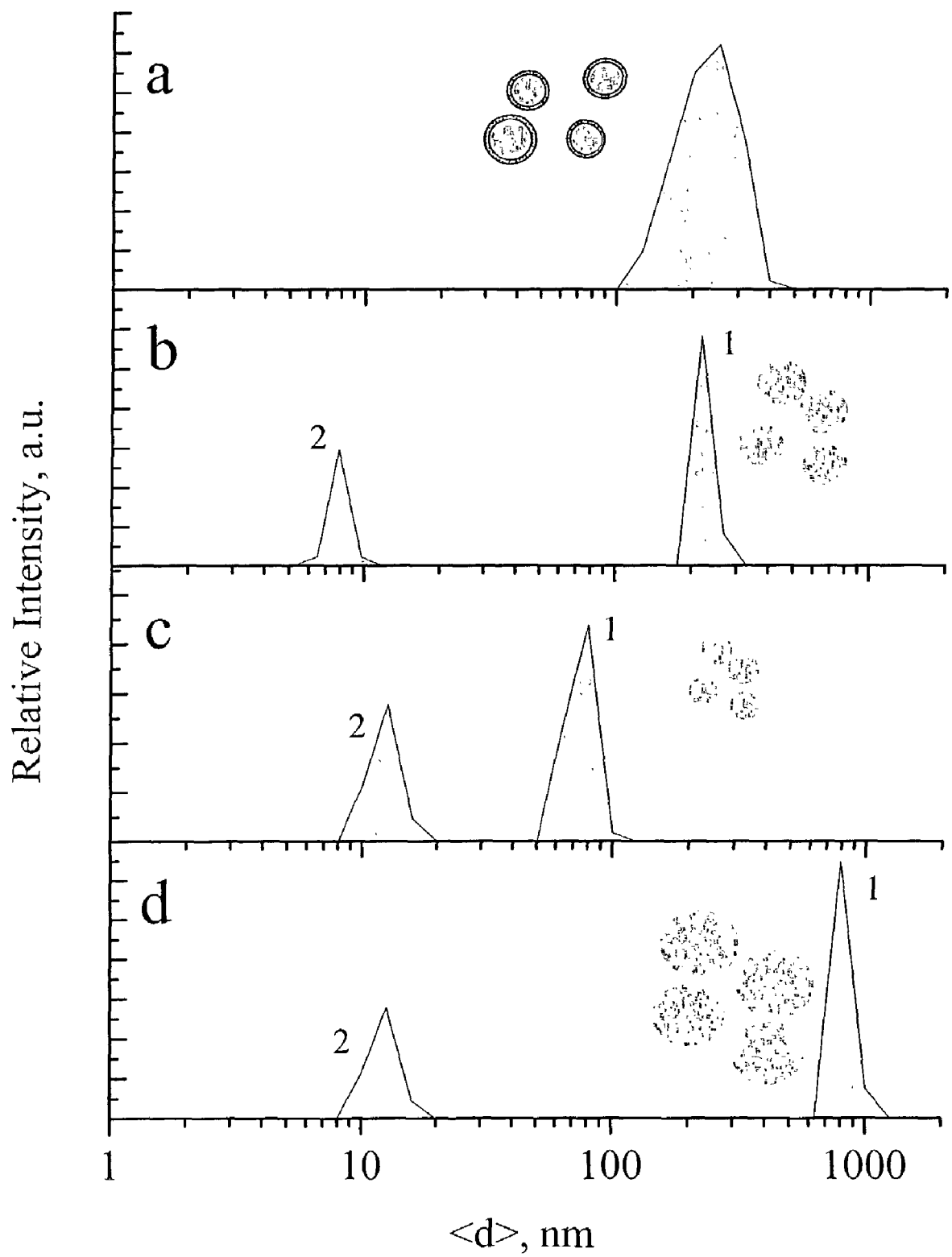
FIGS. 5a-5d are graphs that show size distribution curves for PAAm nanogels encapsulated in liposomes (a) and in buffer (b), the effect of 40 vol. % (c) and 10 vol. % (d) acetone on PAAm hydrogel particles, respectively.

PAAm nanogels may be synthesized using liposomes as reactors as described in §4.2 above. A typical particle size distribution obtained after UV-induced polymerization but before separating hydrogel particles from the liposomes is shown in FIG. 5a. The size distribution is unimodal but relatively wide. After adding 15 mM $T_{X-100}$ and mixing for 5-10 minutes, a peak for large particles (~200 nm) and a peak for small particles (~9 nm) is obtained as shown in FIG. 5b. The total scattering intensity decreased more than ten-fold, indicating that adding the detergent resulted in solubilization of the phospholipid bilayer. The smaller particles are the mixed micelles depicted in FIG. 5b.

To identify the larger particles as pure PAAm hydrogel particles, the ability of a hydrogel to swell or shrink in response to environmental conditions may be exploited. Poly(acrylamide) gels are not temperature- or pH-sensitive, but it has been observed that PAAm gels in water-acetone mixtures may swell (or collapse) as a function of the acetone concentration. In particular, it has been shown that the gel swells at concentrations less than 37 vol. % of acetone and collapses at concentrations greater than 37 vol. % of acetone. The size of phospholipids, on the other hand, is relatively unaffected by acetone concentrations.

An increase of acetone to 40 vol. % resulted in a shift of the PAAm nanogels' 200 nm-peak to smaller sizes, as shown in FIG. 5c, which translates into $\alpha \approx 0.045$. At an acetone concentration of 10 vol. %, however, a volume increase of the PAAm nanogels by a factor 45 was observed, as shown in FIG. 5d. The mixed detergent/phospholipid micelles sizes increased from 9 to 12 nm in response to adding acetone (See FIGS. 3c and 3d). This may be the result of less polar acetone molecules penetrating into the non-polar interior of micelles, leading to the formation of microemulsions. Thus, nanogels may be synthesized within liposomal reactors that are removed by solubilization of the lipid bilayer.

Note that the observed volume changes of these hydrogel particles are much greater than those associated with PAAm macrogels. The swelling ratio of macrogels changes over a long time (time scale: days) to approach some equilibrium value (aging phenomenon). Nanometer-size hydrogel particles, on the other hand, can reach the maximal capability of swelling/deswelling within the observation time scales used in these experiments (30 min).

§4.3.2.2 PNIPA NANOGEL

Figure 6:
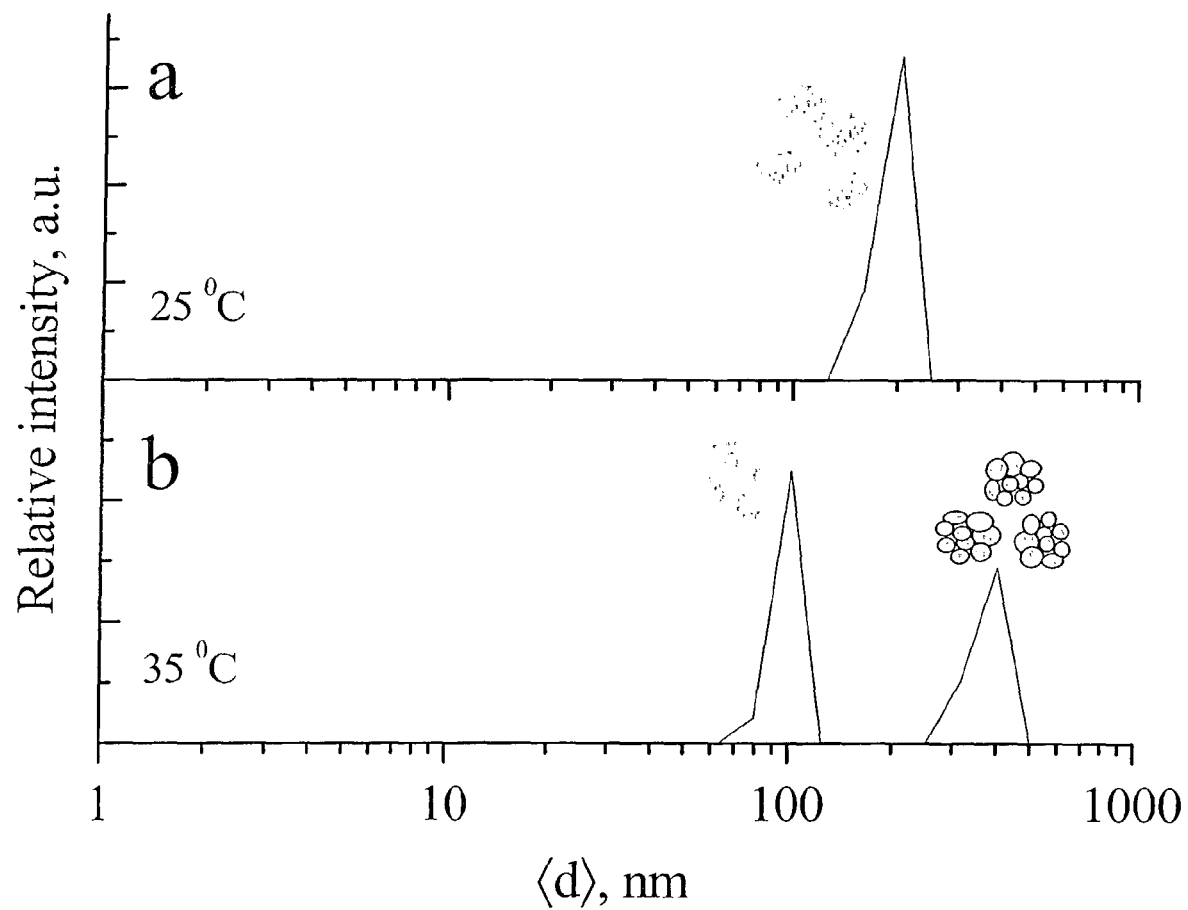
FIGS. 6a and 6b are graphs that show size distribution curves for pure PNIPA hydrogel particles in water below and above the volume phase transition temperature, respectively.
Figure 7:
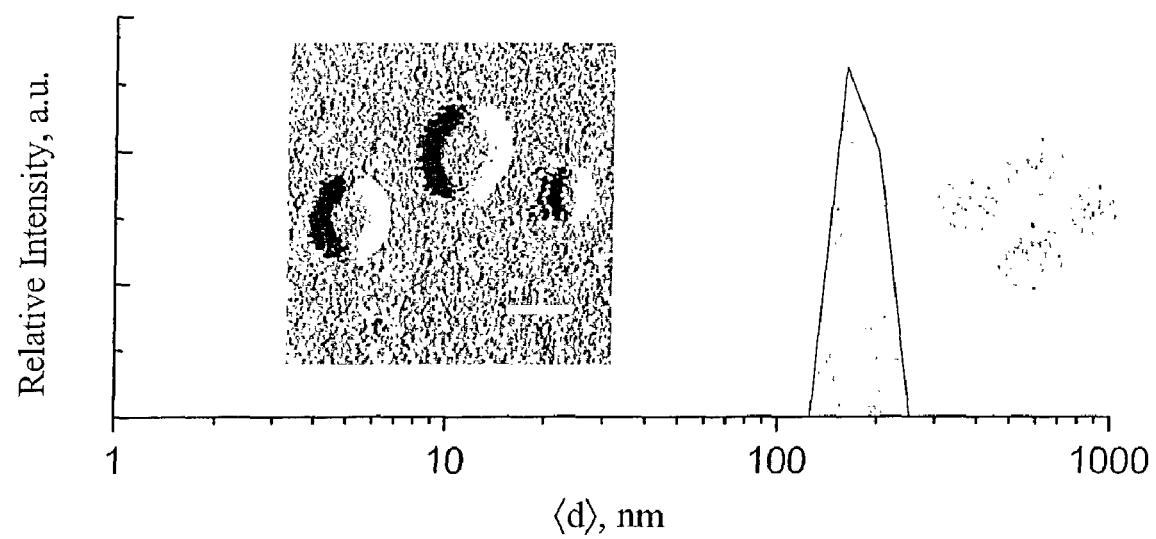
FIG. 7 is a graph that shows the size distribution curve and AFM imaging (amplitude data: bar=200 nm) for pure PNIPA hydrogel particles in water below the volume phase transition temperature.

PNIPA nanogels may be synthesized using liposomes as reactors as described in §4.2 above. As shown in FIGS. 6a and 7, the average diameters of such PNIPA nanogels were around 200 nm and 180 nm, respectively. FIG. 6b shows two peaks in a concentrated solution of PNIPA nanogels above $T_V$. If the peak at ~98 nm is the average diameter of the shrunken beads, the swelling ratio $\alpha$ is around 0.13. The peak for the larger particles at ~398 nm represents aggregates of collapsed hydrogel particles.

Note that, despite aggregation, the solution remains stable and transparent indicating that the aggregates are still colloidally stable in the time scale of interest. Colloid stability depends on the balance of the van der Waals attraction and the electrostatic repulsion. Below $T_V$, PNIPA nanogels are colloidally stable because the gel matrix is hydrated and therefore the van der Waals attractive forces between particles are relatively small. Electrostatic repulsion is also small, as was indicated by the low electrophoretic mobility of the PNIPA microgel. Above $T_V$, the water content of the gels is reduced, giving a higher matrix density and greater attractive forces between the hydrogel particles. At elevated temperatures, the PNIPA microgels are stable only at low electrolyte concentrations. At low ionic strengths, the electrophoretic mobility of PNIPA microgels is high, indicating that electrostatic stabilization can take place. Furthermore, disruption of the hydrodynamic shell around the gel particles with an increasing temperature will promote aggregation as well. The inventors believe that the surface of the shrunken PNIPA hydrogel particles is more hydrophobic than the swollen ones. Aggregation will reduce the total hydrophobicity by decreasing the total surface of the particles. The fine balance of the van der Waals forces and the electrostatic forces may determine the resultant size of the aggregates. If both forces are weak, large fluctuations of the aggregate size can occur.

§4.3.2.3 PNIPA-VI NANOGEL

PNIPA-VI nanogels may be synthesized using liposomes as reactors as described in §4.2 above. Hydrophobic modification of the nanogel's surface increases its sensitivity to pH and ions. As shown in FIG. 6a, the PNIPA-VI nanogels had an average diameter of ~150 nm at pH 7.5 and 25° C. The pH was reduced to 2.5 to confirm that the ionizable VI monomers actually were incorporated within the PNIPA network. Such an acidic environment should result in ionized $=NH^+Cl^-$ groups in the gel particles. FIG. 6b shows that size of PNIPA-VI hydrogel particles at pH 2.5 increased (to ~250 nm) compared to the gel particles with the nonionized =N— groups at pH 7.5. The estimated swelling ratio of α≈4.6 demonstrates the pH-sensitivity of the prepared PNIPA-VI nanogels.

The pH dependence of the diameter for pure PNIPA-VI nanogels (FIG. 7) demonstrates that the diameter of the gel particles increased from 75 nm at pH 6.5 to 128 nm at pH 4.5 (arrow 1) when the neutral imidazolyl groups were converted into the protonated form. The swelling resulted from an imbalance between repulsive electrostatic forces among functional groups attached to the cross-linked polymer (ionic osmotic pressure) and attractive forces of the polymer network (network swelling pressure). The balance between these factors determines the physical dimensions of the hydrogel particles. In other words, in the pH range between 7 and 4.5, the concentration of acidic ions ($H^+$ and $Cl^-$) in the outer solution will increase with decreasing pH. Those ions will be attracted to the gel and will facilitate the imidazolyl groups' protonation. Until all imidazolyl groups are protonated, a decrease in pH will increase the ion swelling pressure. To compensate for this, the polymer network swells. Eventually, all imidazolyl groups will be converted into the saline form according to the following equation:

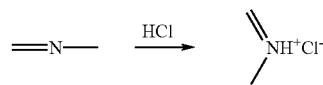

The imidazolyl groups are essentially ionized at pH 4.5. A further decrease in pH will cause excess acidic ions ($H^+$ and $Cl^-$) in the gel and screening of the ionizable groups. The latter phenomenon results in a drop of the ion swelling pressure. Again, to compensate for the decrease, the gel shrinks. A contraction in the pH range from 4.5 to 2 was observed. Interestingly, a subsequent increase in pH (arrow 2) by adding NaOH only resulted in a substitution of excess hydrogen counterions $H^+$ for sodium counterions $Na^+$, so that the screening of the charged species intensified. The physical dimensions of the gels did not return to their maximal size but continued to decrease in the range of pH between 2 and 4.5. This process is analogous to the addition of NaCl when all ionizable groups of imidazole are protonated. Arrow 3 in FIG. 7 shows the corresponding change of the diameter of nanogels upon adding 10 mM NaCl into the gel suspension at pH 4.0. A further increase in pH by adding NaOH (arrow 2) brought the size of the hydrogel particles back to their minimum size at pH 7.0. No significant change in size was observed in the range of pH from 7 to 11 since most imidazolyl groups were already deprotonated. Thus, the data shown in FIG. 7 confirms the pH- and ionic-sensitivities of the PNIPA-VI nanogels from pH 2 to 7. At pH≧6.5, where the ionic- and pH-sensitivities are weak, changes in the nanogels' size can be detected near the temperature of volume phase transition of the polymer, as shown below.

Figure 8:
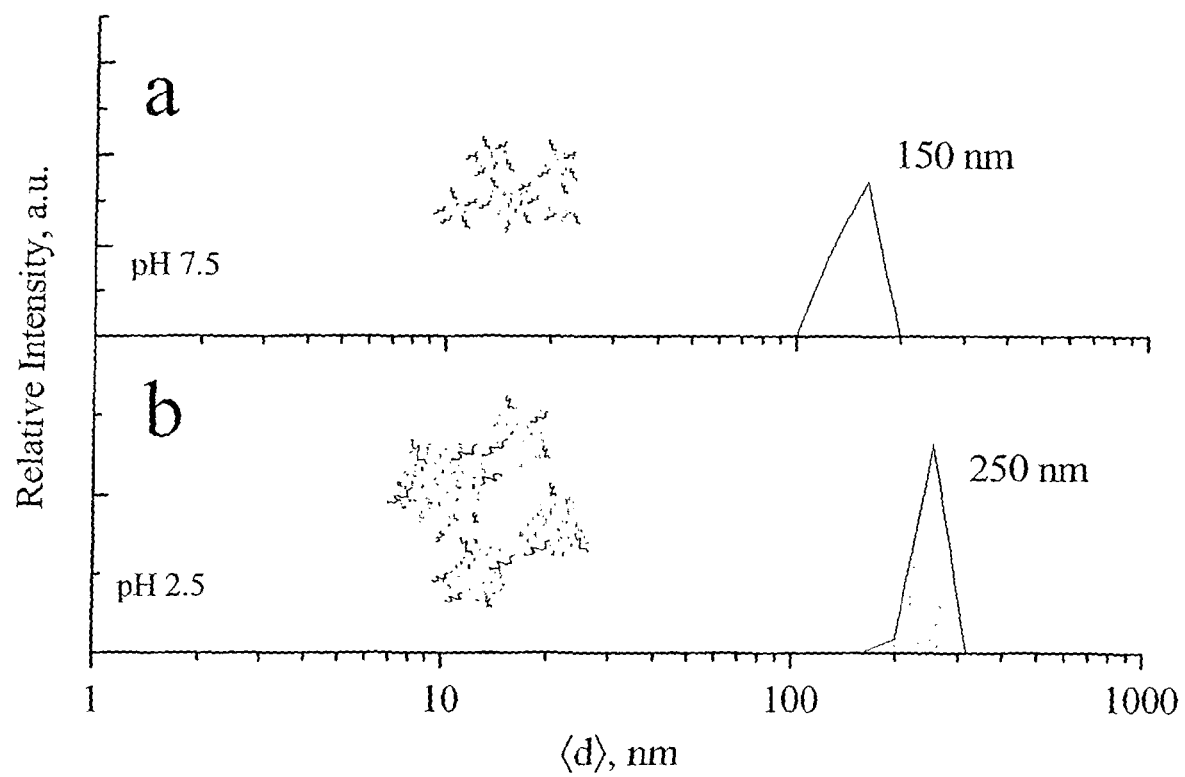
FIGS. 8a and 8b are graphs that show size distribution curves for PNIPA-VI nanogel particles in buffer at pH 7.5 and at pH 2.5, respectively.

FIGS. 8a-c show that the average hydrodynamic diameter of anchored PNIPA-VI hydrogel particles remains almost unchanged between 25° C. and 35° C. at pH 6.5. Above $T_V$≈37° C., hydrophobicity increases due to contraction of the nanogels, which leads to aggregation. This is demonstrated at 40° C., as shown in FIG. 8d. At elevated temperatures, extensive aggregation of collapsed nanogels is in progress, resulting in a bimodal distribution with peaks at higher hydrodynamic diameters than below $T_V$. Upon a further increase in the temperature, a sharp increase of the light scattering intensity was observed, and turbidity of the suspension became so strong that light scattering measurements were impossible.

As shown in FIG. 8c, the aggregation of anchored nanogels was confirmed by its partial irreversibility upon cooling to 35° C. It is likely that restoring the particles' initial size requires a longer time under cooling compared with heating (for the data shown, the equilibration time was ~30 min after the temperature change). Nevertheless, after cooling to 25° C. the size distribution curve for the anchored PNIPA-VI nanogels was restored (See FIG. 8a).

§4.4 CONCLUSIONS

As can be appreciated by the foregoing, the present invention can be used to produce hydrogels using a method that provides more size control and higher yields than previous methods. Since hydrogels with nanoscale diameters can swell or shrink faster in response to environmental changes, the present invention opens up many new potential applications for hydrogels.

What is claimed is:

1. A method for producing hydrogels having a diameter ranging from approximately 30 nm to approximately 1000 nm, the method comprising:
    a) encapsulating hydrogel-forming components into liposomes, wherein the hydrogel-forming components include (A) initiator, cross-linker, and polymer forming monomers, or (B) initiator and cross-linkable polymer-forming monomers; and
    b) polymerizing the hydrogel-forming components by redox- or photo-initiation, thereby forming hydrogel particles, each of the formed hydrogel particles (1) including covalently bonded monomers, and (2) having a diameter ranging from approximately 30 nm to approximately 1000 nm.

2. The method of claim 1 wherein the liposomes are prepared by
    a) forming a lipid film;
    b) obtaining multilamellar vesicles from the lipid film;
    c) freezing-thawing a multilamellar vesicles solution; and
    d) sonicating the multilamellar vesicles solution to prevent a loss of phospholipid.

3. The method of claim 2 power and duration of the act of sonication is regulated to control the size and polydispersity of liposomes, thereby controlling the size and polydispersity of hydrogel particles formed.

4. The method of claim 1 wherein the liposomes are prepared from phospholipids, and wherein the phospholipids are selected from a group consisting of egg yolk L-α-phosphatidylcholine (EPC), 1,2-dimyristoyl-sn-glycero-3-phosphatidylcholine (DMPC), 1,2-dipalmitoyl-sn-glycero-3-phosphatidylcholine (DPPC), 1,2-dioleoyl-sn-glycero-3-phosphatidylcholine (DOPC), 1,2-distearoyl-sn-glycero-3-phosphatidylcholine (DSPC), 1,2-dilauroyl-sn-glycero-3-phosphatidylcholine (DLPC), 1,2-dioleoyl-sn-glycero-3-phosphaethanolamine (DOPE), 1-paimitoyl-2-oleoyl-sn-glycero-3-phosphaethanolamine (POPE), 1,2-dimyristoyl-sn-glycero-3-phosphaethanolamine (DMPE), 1,2-dipalmitoyl-sn-glycero-3-phosphaethanolamine (DPPE), and 1,2-distearoyl-sn-glycero-3-phospharthanolamine (DSPE).

5. The method of claim 4 wherein the phospholipids are mixed with a sterol to stabilize the phospholipid bilayer.

6. The method of claim 5 wherein the sterol is a cholesterol.

7. The method of claim 1 wherein the polymer-forming monomers include monomers containing a vinyl-group.

8. The method of claim 7 wherein the polymer-forming monomers containing a vinyl-group are selected from a group consisting of acrylamide, N-isopiopylacrylamide, N,N-dimethylacrylamide, N,N-dietlylacrylamide, 1-vinylimidazole, sodium acrylate, sodium methacrylate, 2-hydroxyethyl-methacrylate (HEMA), N,N-dimethylaminoethyl methacrylate (DMAEMA), N-[tris(hydroxymethyl)methyl]acrylamide, 1-(3-methacryloxy)propylsulfonic acid (sodium salt), allylamine, N-acryloxysuccinimide, N-vinylcaprolactam, 1-vinyl-2-pyrrolidone, 2-acrylamido-2-methyl-1-propane-sulfonic acid (sodium salt), (3-acrylamidopropyl) trimethylammonium chloride, and diallyldimethylammonium chloride.

9. The method of claim 1 wherein the hydrogel-forming components include biocompatible polymers selected from a group consisting of methacrylated or hydrcxyethyl-methacrylated water soluble non-ionic or ionic polysaccharides (For example, methacrylated dextran ("dex-MA"), hydroxyethyl-methacrylated dextran ("dex-HEMA"), methacrylated pullulan, and hydrcxyethyl-methacrylated pullulan), poly(ethylene glycol) monomethacrylate, or poly(ethylene glycol) diacrylate).

10. The method of claim 1 wherein the hydrogel-forming components include biodegradable polymers selected from a group consisting of triblock copolymer of poly(lactic acid)-poly(ethylene glycol)-poly(lactic acid) end-capped with acrylate or methacrylate functionalities, grafted copolymers of poly(lactic acid)-poly(vinyl alcohol) end-capped with acrylate or methacrylate functionalities, and (oligolactae)-hydroxyethyl methacrylated dextran [dex-(lactate-)HEMA].

11. The method of claim 1 wherein the cross linkers are selected from a group consisting of N,N'-methylenebisacrylamide, N,N'-(1,2-dihydroxyethylene)bisacrylamide, ethylene glycol diacrylate, di(ethylene glycol) diacrylate, tri(ethylene glycol) diacrylate, tetra(ethylene glycol) diacrylate, ethylene glycol dimethacrylate, di(ethylene glycol) dimehacrylate, tri(ethylene glycol) dimethacrylate, tetra(ethylene glycol) dimethacrylate, and pentaerythritol triacrylate.

12. The method of claim 1 wherein the act of photoinitiation is accomplished by a photoinitiator selected from a group consisting of 2,2-diethoxyacetophenone, 2,2-dimethoxy-2-phenylacetophenone (IRGACURE 651), 1-[4-(2-hydroxyethoxy)phenyl]-2-hydroxy-2-methyl-1-propan-1-one (IRGACURE 2959), 2-hydroxy-2-methylpropiophenone, and 2-hydroxy-4'-(2-hydroxyethoxy)-2-methylpropiophenone.

13. The method of claim 1 wherein the act of redox initiation is accomplished at temperatures between 45 and 75° C.

14. The method of claim 1 wherein the act of redox initiation is accomplished by a redox initiator, the redox initiator selected from a group consisting of ammonium persulfate, potassium persulfate, 2,2'-azobis[2-methyl-N-(2-hydroxyethyl)propionamide (VA-086), 2,2'-azobis(2-amidinopropane)dihydrochloride (V-50), 4,4'-azobis(4-cyanovaleric acid).

15. The method of claim 1 wherein hydrophobic chains are immobilized onto the surface of hydrcgel particles.

16. The method of claim 15 wherein the act of immobilizing hydrophobic chains onto the surface of hydrogel particles includes
   i) embedding water-insoluble hydrophobic monomers in the liposome's lipid bilayer; and
   ii) co-polymerizing the water-insoluble hydrophobic monomers with the polymer-forming monomers, thereby forming hydrogel particles with hydrophobic chains immobilized on their surfaces.

17. The method of claim 15 wherein the hydrophobic monomers are selected from a group of N-alkylacrylamides such as N-octadecylacrylamide, N-dodecylacrylamide, N-octylacrylamide.

18. The method of claim 1 further comprising:
   c) diluting large unilamellar vesicles (LUV) suspension before polymerization to prevent polymerization outside the liposomes.

19. The method of claim 1 further comprising:
   c) including polymerization inhibitor in the solution outside the liposomes.

20. The method of claim 19 wherein the polymerization inhibitor is selected from a group consisting of hydroquinone (HQ), hydroquinone monoinethylether (MEHQ), and N,N'-di-sec-butyl-p-phenylenediamine.

21. The method of claim 1 further comprising
   c) separating the hydrogel particles from the liposomes.

22. The method of claim 21 wherein the act of separating the hydrogel particles from the liposomes includes
   i) solubilizing the lipid bilayer using detergent.

23. The method of claim 22 wherein the detergent is selected from a group consisting Triton X-100, n-octyl-b-D-glucopyranoside, n-octyl-tetraoxyethylene (POE4), n-hexyl-glucopyranoside, n-heptyl-glucopyranoside, cholic acid (sodium salt), glycocholic acid (sodium salt), deoxycholic acid (sodium salt), taurocholic acid (sodium salt , chenoxycholic acid (sodium salt), and sodium dodecyl sulfate (SDS).

24. The method of claim 21 wherein the act of separating the hydrogel particles from the liposomes includes
   i) adding phospholipases to degrade and solubilize the liposomes.

25. The method of claim 24 wherein the phospholipases are selected from a group consisting of phospholipase $A_2$ ($PLA_2$), phospholipase C (PLC), and phospholipase D (PLD).

26. The methOd of claim 24 wherein further comprising
   ii) removing the products of the phospholipid bilayer solubilization, including mixed phospholipid-detergent micelles.

27. The method of claim 26 wherein the products of the phospholipid bilayer solubilization, including mixed phospholipid-detergent micelles, are removed by dialysis.

28. The method of claim 21 further comprising
   d) drying the hydrogel particles.

29. The method of claim 28 wherein the act of drying the hydrogel particles is performed by evaperation in temperature gradient under vacuum while flashing with nitrogen.

30. The method of claim 29 wherein the temperature gradient is between −77 and 30° C.

31. The method of claim 28 wherein the act of drying the hydrogel particles is performed by freeze-drying (lyophilic drying).

32. The method of claim 1 wherein the act of polymerization of the hydrogel-forming components causes covalent cross-linking.

33. The method of claim 1 wherein the act of encapsulating hydrogel-forming components into liposomes occurs before the act of polymerizing the hydrogel-forming components.

34. The method of claim 1 wherein the act of encapsulating hydrogel-forming components into liposomes does not, itself, initiate polymerizing the hydrogel-forming components.

* * * * *